(12) United States Patent
Buchanan

(10) Patent No.: US 9,750,582 B1
(45) Date of Patent: Sep. 5, 2017

(54) ENDODONTIC THERAPY SYSTEM, APPARATUS AND METHOD MAKING USE OF A DISPOSABLE CT REGISTRATION TRAY DEVICE WITH PRE-SET RADIOGRAPHIC REGISTRATION MARKERS

(71) Applicant: L. Stephen Buchanan, Santa Barbara, CA (US)

(72) Inventor: L. Stephen Buchanan, Santa Barbara, CA (US)

( * ) Notice: Subject to any disclaimer, the term of this patent is extended or adjusted under 35 U.S.C. 154(b) by 13 days.

(21) Appl. No.: 14/734,811

(22) Filed: Jun. 9, 2015

Related U.S. Application Data

(60) Provisional application No. 62/009,725, filed on Jun. 9, 2014.

(51) Int. Cl.
| | | |
|---|---|---|
| *A61B 6/14* | (2006.01) | |
| *A61C 5/02* | (2006.01) | |
| *A61C 9/00* | (2006.01) | |
| *A61B 6/04* | (2006.01) | |
| *A61B 6/03* | (2006.01) | |
| *A61B 19/00* | (2006.01) | |

(52) U.S. Cl.
CPC .............. *A61C 5/02* (2013.01); *A61B 6/032* (2013.01); *A61B 6/0492* (2013.01); *A61B 6/14* (2013.01); *A61B 19/54* (2013.01); *A61C 9/0006* (2013.01); *A61B 2019/5466* (2013.01)

(58) Field of Classification Search
CPC ................................ A61C 9/0006; A61B 6/14
See application file for complete search history.

(56) References Cited

U.S. PATENT DOCUMENTS

| | | |
|---|---|---|
| 6,948,936 B2 | 9/2005 | Miller et al. |
| 7,361,020 B2 | 4/2008 | Abolfathi et al. |
| 8,750,590 B2 | 6/2014 | Greenberg |
| 2012/0230567 A1* | 9/2012 | Greenberg ............... A61B 6/14 382/131 |

FOREIGN PATENT DOCUMENTS

| | | |
|---|---|---|
| WO | 02053056 | 7/2002 |
| WO | 2005055856 | 6/2005 |

* cited by examiner

*Primary Examiner* — Eric D. Bertram
(74) *Attorney, Agent, or Firm* — GableGotwals

(57) ABSTRACT

A system for endodontic therapy includes a radio-opaque tray having three or more fiduciary markers embedded in the tray, a leveling device, and one or more bite stops arranged to ensure maintenance of adequate bite registration or impression material between opposing teeth to allow 3D reconstruction of occlusal surfaces.

9 Claims, 6 Drawing Sheets

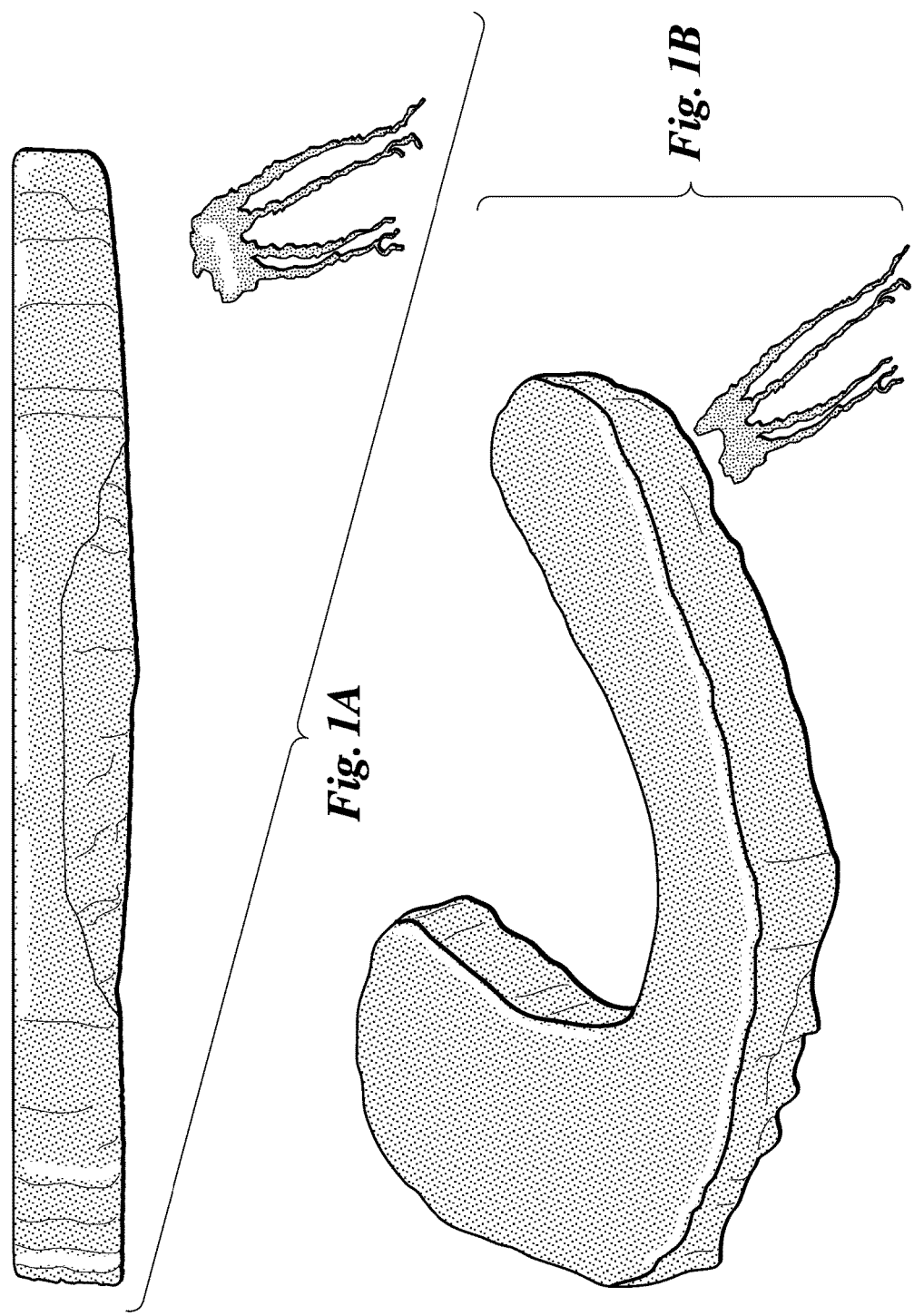

ENDODONTIC THERAPY SYSTEM, APPARATUS AND METHOD MAKING USE OF A DISPOSABLE CT REGISTRATION TRAY DEVICE WITH PRE-SET RADIOGRAPHIC REGISTRATION MARKERS

BACKGROUND OF THE INVENTION

This invention generally relates to endodontic therapy systems, apparatuses and methods that make use of bite registration or impression trays. More specifically, the invention relates to a system that helps technicians ideally position a patient's head prior to a cone beam computerized tomography ("CBCT") capture for the purpose of designing and fabricating drill guides used in minimally invasive implant surgery, root canal treatment, or endodontic surgery.

Endodontic therapy is done to eliminate degenerating pulp tissue and infection from inside dental root structure in order to maintain or return the health of the periodontal supporting structures surrounding said tooth. X-ray imaging allows dentists to visualize the mineralized anatomic structures below the surface of gum and tooth structure to look for signs of decay, failure of previous restorative work, and infection associated with endodontic disease, periodontal disease, or root fractures. Dental radiography, if treatment is needed, also informs the dentist of the morphology of the roots and the root canal systems inside of them. Unfortunately, traditional two-dimensional PA radiographic methodology obscures anatomic detail and dental pathosis due to the superimposition of all bone and tooth structure in a given x-ray plane.

Recently, CBCT has been introduced to dentistry, revolutionizing clinical diagnosis, treatment planning, and treatment execution. The single shortcoming of CBCT imaging is the beam-hardening artifacts that occur adjacent to radio-dense dental materials and objects including but not limited to stainless steel posts in roots, cast-metal crowns, and silver fillings. This artifacted coronal zone ("ACZ") is generally acceptable to dentists because these are the soft and hard tissues that can be examined directly with adequate light and magnification and because conventional periapical radiographs can often show decay underneath fillings and the margins of crowns.

There are two applications, however, where it is critical to have an accurate representation of the tooth and gingival structures typically obscured in the ACZ of CBCT reconstructions. The first, and the most common, application is when CAD/CAM fabrication of dental prostheses is planned. In that case the external hard and soft tissue contours are captured with analog or digital impressioning methods alone as bone or root structure are not directly related to that treatment plan.

The second application is when drill guides are to be designed and fabricated for minimally-invasive implant surgery, root canal treatment, or endodontic surgery. To accomplish this, an analog or digital impression of the patient's teeth is taken. From this, an acrylic scanning appliance is fabricated on either the plaster model created from a traditional impression or on a polymer model generated from digital impressioning (or scanning a plaster model of the patient's teeth) and 3D printing. The scanning appliance has three or more radiographic registration markers—such as glass beads—attached at various positions around the outward and inward perimeters of the appliance so that the markers that can be easily seen without causing artifacts when the appliance is scanned.

The scanning device is then placed in the patient's mouth, onto their teeth, and a CBCT scan is captured. As usual, in this first volume the teeth and gingiva are obscured in the ACZ. However, the jaws and teeth above and below the ACZ are represented without artifact, as are the registration markers on the inside and outside perimeters of the scanning appliance. Then the appliance is scanned alone, on a stand in the center of the machine's rotational scanning path.

This second (appliance alone) volume is different than the first (in-mouth) volume—it is without artifact, and because the registration markers on the appliance reconstruct without artifact in both volumes, it becomes possible to superimpose the two volumes by aligning the same markers in each. After this the ACZ is subtracted from the first scan of the patient and is replaced with the tooth and gingiva map from the second scan thereby creating, in essence, a holistic digital model of all the patient's soft and hard tissues.

The greatest obstacle to mass market acceptance of CT-guided cutting procedures in dentistry is the time, effort, and expense currently required to create CT-based drill guides for implant surgery. The preferred embodiments of the invention described in this application are an improvement over the prior art as it eliminates the need for a separate laboratory procedure, the cost of that procedure, and the need for a second appointment to complete the imaging. This invention also helps CT technicians ideally position the patient's head prior to the CBCT capture to minimize the height of the artifacted coronal zone and maximize the anatomy seen around that zone. Last, any dental lab or office with 3D printing capability can print the drill guide suggested by the scans.

SUMMARY OF THE INVENTION

An endodontic therapy system and method according to this invention includes:
1. a disposable bite registration tray with at least three radiographic registration or fiduciary markers preferably positioned around the tray's inner and outer borders to aid superimposition of subsequent computerized tomography ("CT") scans of a patient having the tray in place;
2. a leveling device to help minimize the height of the artifacted coronal zone ("ACZ") and ensure the patient is not positioned in a manner that will unnecessarily increase the height of the ACZ;
3. a tooth or bite stop to hold the opposing dentition apart during the registration/impressioning procedure to maintain an adequate thickness of material between those surfaces; and
4. a scan volume indicator to insure inclusion of the desired anatomy in the planned scan.

The fiduciary markers, bite stops, and leveling device do not artifact any of the scanned data.

The objectives of the include providing a system and method that (1) eliminates the need for a separate laboratory procedure and a second appointment to complete the imaging; (2) helps CT technicians ideally position the patient's head prior to the CBCT capture to minimize the height of the ACZ and maximize the anatomy seen around that zone; (3) facilitates a dental lab or office with 3D printing capability printing the drill guide suggested by the scans; and (4) reduces the amount of time and cost associated with making a drill guide.

BRIEF DESCRIPTION OF THE DRAWINGS

FIG. 1A is a front view of a preferred embodiment of a scanning appliance in virtual space relative to the root canal system of tooth #18 (segmented using MIMICS® software for medical image processing (Materialise, Belguim)).

FIG. 1B is an isometric view of the scanning appliance relative to FIG. 1A.

ELEMENTS AND NUMBERING USED IN THE DRAWING FIGURES

Figure 2A:
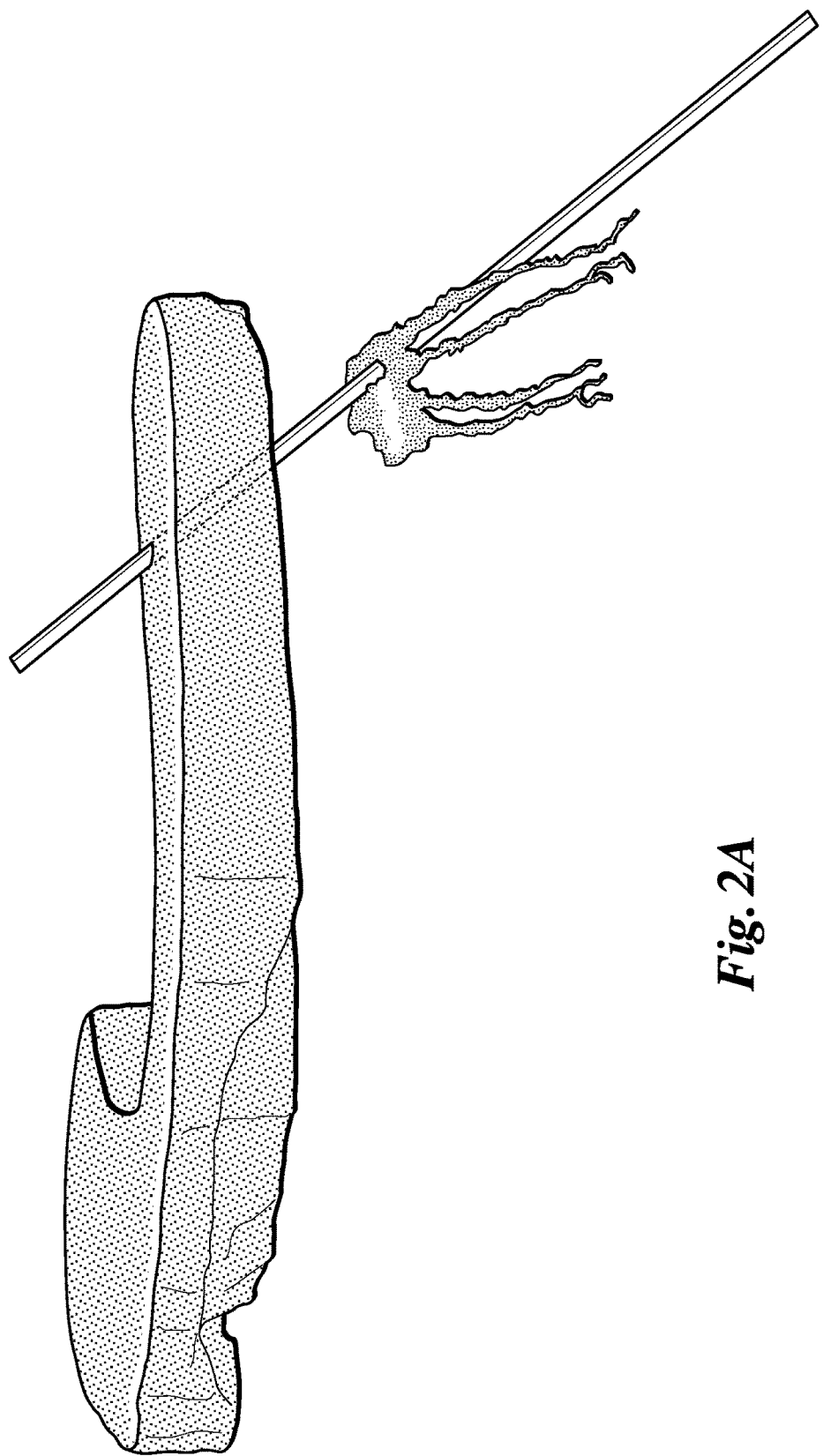
FIG. 2A is a view of the scanning appliance of FIG. 1A showing the access path to DB canal orifice, with the treatment-planned virtually, to enter each root canal at an ideal angle (see also FIGS. 2B to 2D).
Figure 2B:
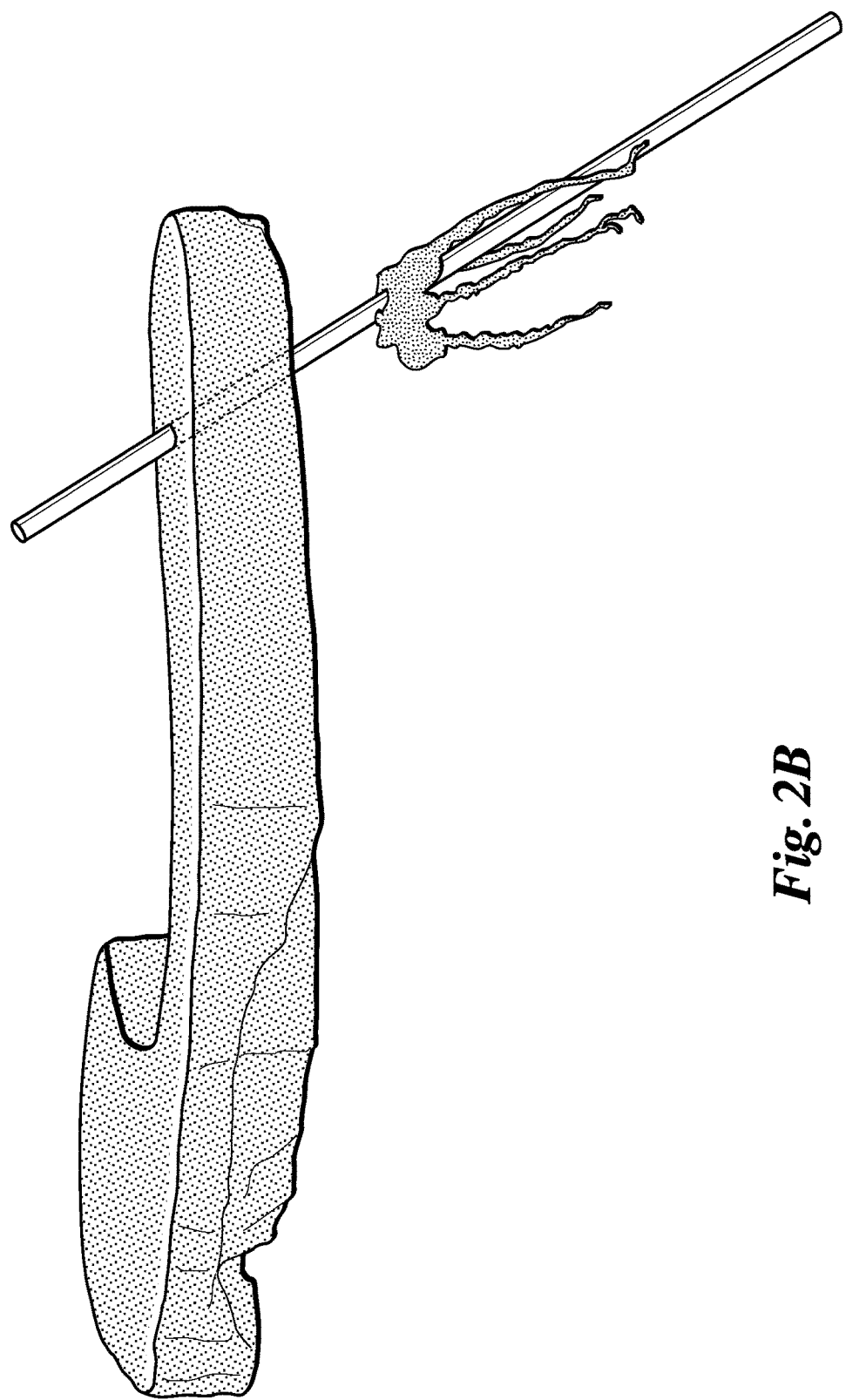
FIG. 2B is a view of the scanning appliance of FIG. 1A showing the access path to DL canal orifice.
Figure 2C:
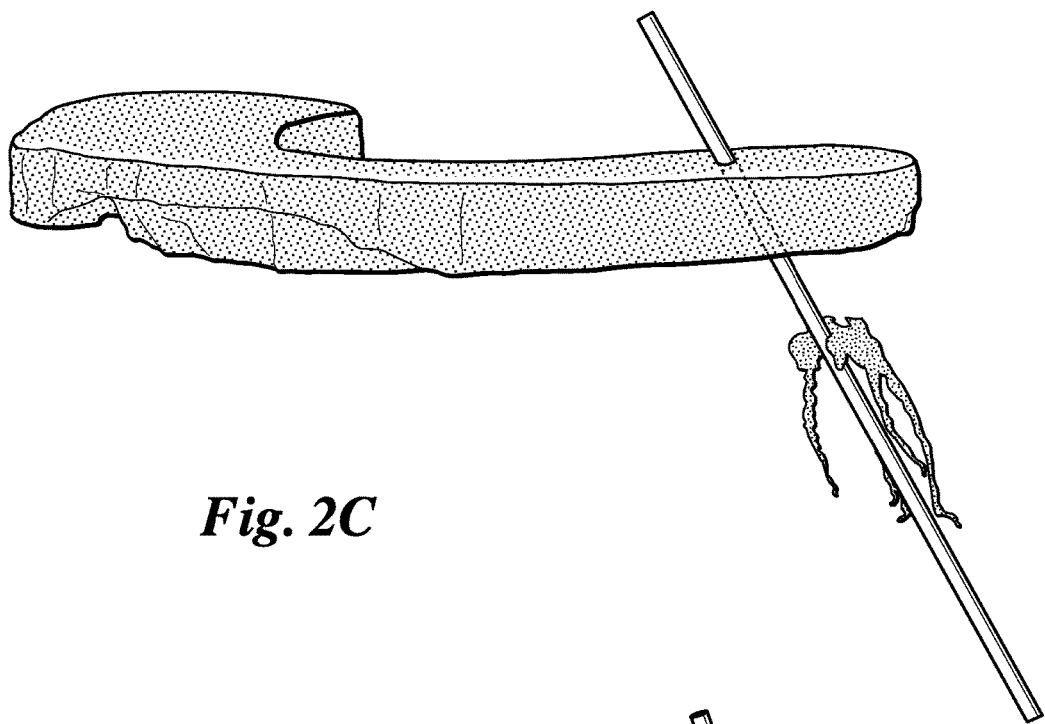
FIG. 2C is a view of the scanning appliance of FIG. 1A showing the access path to MB canal orifice.
Figure 2D:
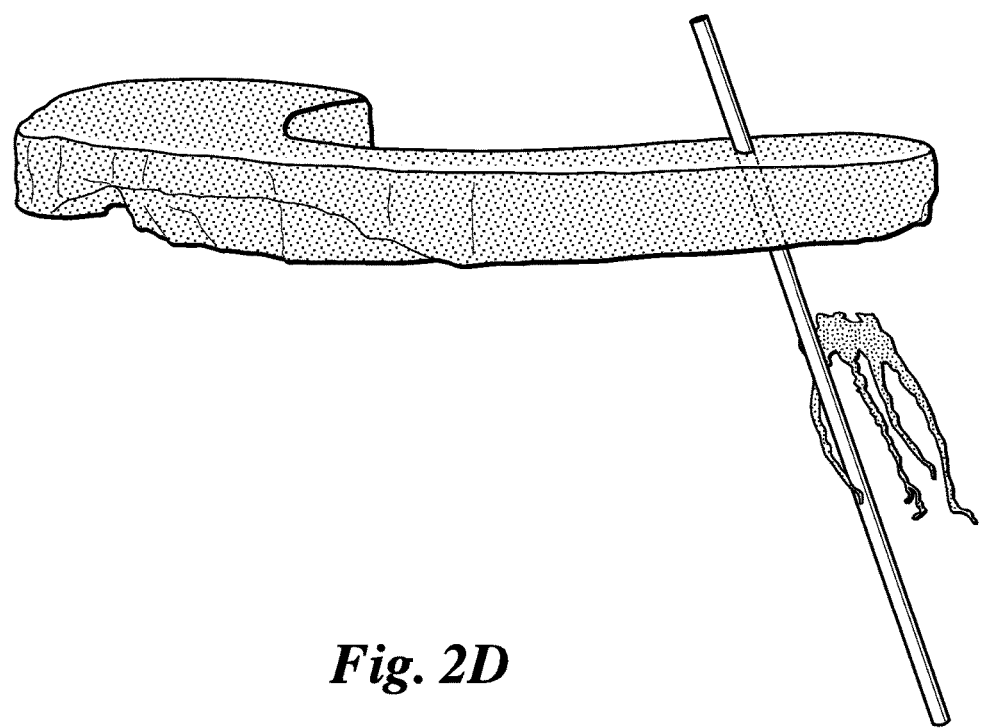
FIG. 2D is a view of the scanning appliance of FIG. 1A showing the access path to ML canal orifice.
Figure 3A:
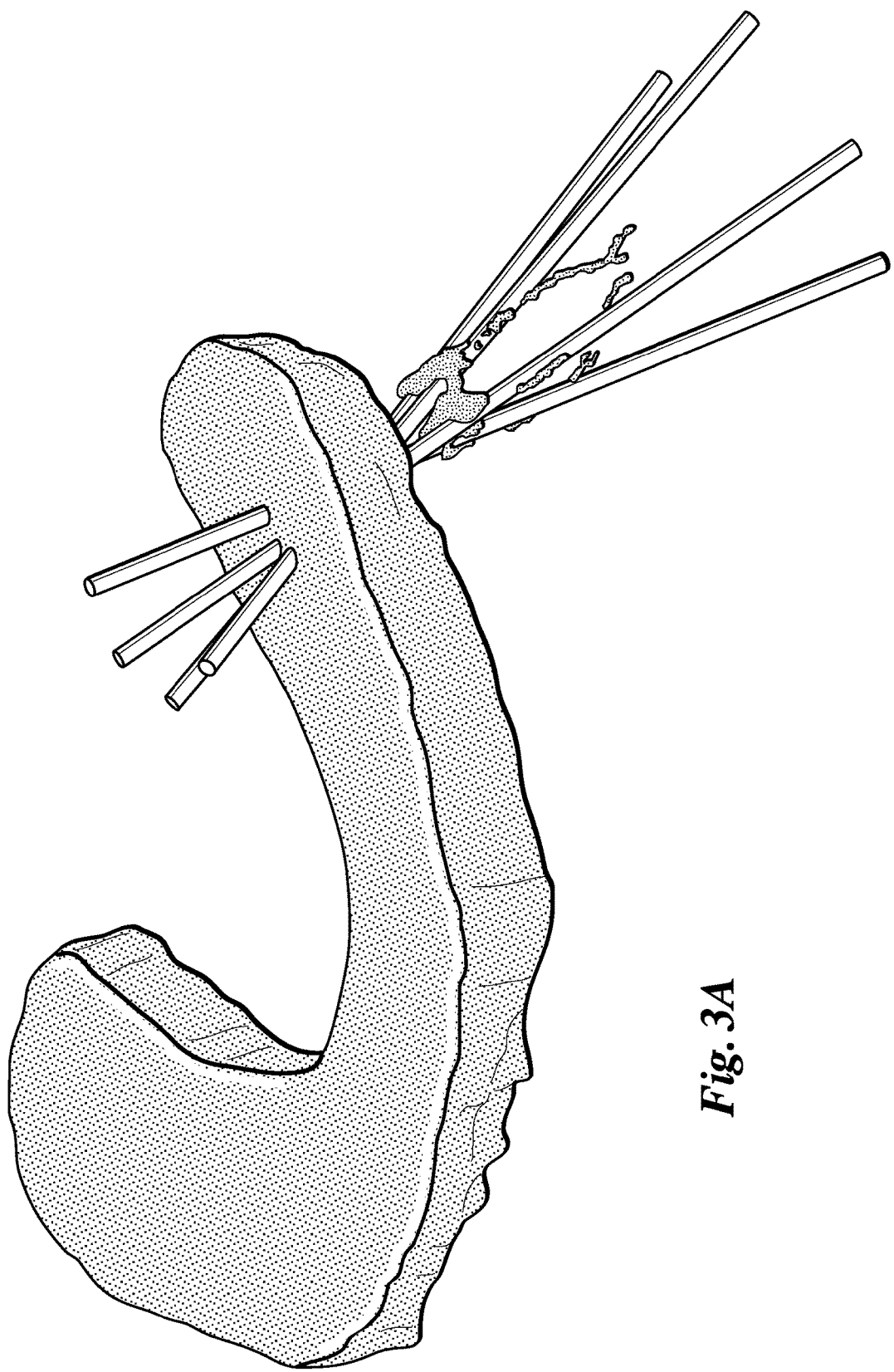
FIG. 3A is a view of the scanning appliance of FIG. 1A showing four minimally invasive access paths to each of the root canals (see also FIGS. 2A to 2D).
Figure 3B:
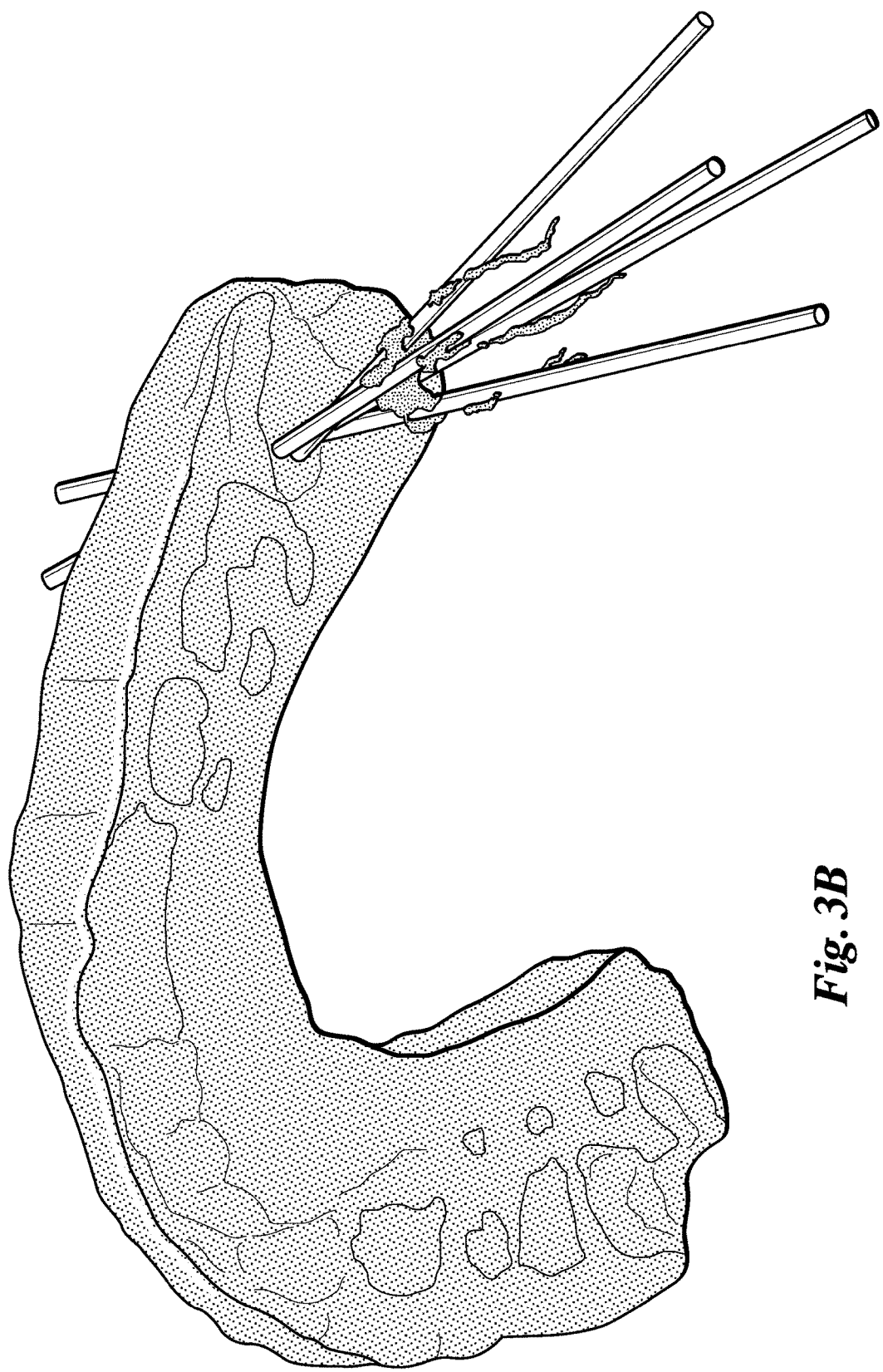
FIG. 3B shows the underside of the scanning appliance of FIG. 1A, showing the access paths seen in FIG. 3A intersecting the occlusal surface of tooth #1.

101 Disposable CT Registration Tray
102 Registration markers
103 Tray handle
104 Leveling bubble
105 Bite stop
106 Syringed bite registration or impression material in tray
107 Cross-section of disposable CT registration tray between opposing teeth embedded in bite-registration or impression material

DETAILED DESCRIPTION OF THE PREFERRED EMBODIMENTS

The current method using prior art systems and apparatuses is shown in Table 1.

TABLE 1

| Prior Art Method. | |
| --- | --- |
| Dentist | Dental Lab |
| 1. Perform a CT scan | |
| 2. Take upper and lower impressions | |
| 3. Send the impressions to a lab | |
| | 4. Pour impressions, and separate, grind, and articulate model |
| | 5. Design and fabricate acrylic scanning appliance with fiduciary markers |
| 6. Take second CT scan with the scanning appliance in the patient's mouth (the first scan is needed to diagnose the case before CT-GES treatment planning can be considered) | |

Using the system and apparatuses of this invention, the prior art method is replaced by a single scan of a bite registration tray when in the patient's mouth. The turn-around time from first imaging to perfect access is at least halved, costs are at least halved and, because of the quick turn-around time and lower cost, CT-guided implant surgery is encouraged.

Because coronal structures cannot be seen with CT, this data must be captured by other means to have a full and accurate computer model of the crowns of teeth as those crowns relate to root structures (which can be seen on a CT). If the impression material chosen for the CT scan is radio-opaque, the dental lab procedure currently needed to create a scan appliance can be eliminated. In effect, the CT-leveling bite-plane provided by the bite registration tray of this invention is the CT scanning appliance.

First, the bite registration tray is inserted into a tab on a level-scan device of a kind typically used for CT scanning. Second, one or both sides of the tray is loaded with bite registration paste (or covers are peeled off which expose pre-placed bite registration paste). Third, the patient is guided to close his or her teeth into the registration paste with the mandible set in centric position (the mandibular condyles are moved to their mid-most, rear-most, and upper-most position in the joint space). This provides impressions of the occlusal surfaces. Those impressions are the only ones needed to make drill guides for implants and endodontic access. Impressions of the sides or gingival contours are not needed.

A registration tool aligns, using at least three and preferably up to nine fiduciary markers or points, the first CT-scan data set (patient with scanning appliance in place) and the second CT-scan data set (scanning appliance only). The fiduciary markers are any radio-opaque material preferable, including but not limited to gutta percha.

A snap-line tool attaches a starting point to each canal orifice in the axial plane, and then allows each of those points to be elongated as lines in the X and Y-slice angles to provide ideal access entry paths. The drill guide design is aided through software that locates the guide ring on the outside of the drill guide—an exact distance from the final length of the drill—so the Z-plane can be controlled as well.

Software suitable for i-Dixel CT-GEA registration and treatment planning permits a clinician to CT-capture a patient's jaw with the scanning appliance in place, scan the appliance separately, register the two datasets, treatment plan the access path or paths, and email the access path plan to a local digital dental lab which sets up and 3-D prints the needed drill guides.

What is claimed:

1. A system for endodontic therapy, the system comprising:
a scanning appliance including a radio-opaque tray including three or more fiduciary markers embedded in the tray, a leveling device arranged to limit a height of an artifacted coronal zone, and one or more bite stops, and
a virtual endodontic treatment plan including a scan of the scanning appliance and at least one access path to a root canal,
the bite stops arranged to ensure maintenance of adequate bite registration or impression material between opposing teeth.

2. A system according to claim 1 wherein the three or more fiduciary markers are located on an inside or outside surface of the tray.

3. A system according to claim 1 wherein each fiduciary marker, the leveling device, and the one or more bite stops do not artifact or appear on a scanned image.

4. A system according to claim 1 wherein the leveling device is a bubble.

5. A system according to claim 1 further comprising an aiming device arranged to show a boundary of a canal volume.

6. A system for endodontic therapy, the system comprising:
- a scanning appliance including a radio-opaque tray including three or more fiduciary markers embedded in the tray, a leveling device, and one or more bite stops;
- a virtual endodontic treatment plan including a scan of the scanning appliance and at least one access path to a root canal; and
- an aiming device arranged to provide a starting point to a canal orifice in an axial plane and elongate each of those starting points as lines in X and Y-slice angles to form the access path,
- the bite stops arranged to ensure maintenance of adequate bite registration or impression material between opposing teeth.

7. A system according to claim 6 wherein the three or more fiduciary markers are located on an inside or outside surface of the tray.

8. A system according to claim 6 wherein each fiduciary marker, the leveling device, and the one or more bite stops do not artifact or appear on a scanned image.

9. A system according to claim 6 wherein the leveling device is a bubble.

* * * * *